United States Patent
Smith et al.

(10) Patent No.: US 7,253,302 B2
(45) Date of Patent: *Aug. 7, 2007

(54) MIXED ESTERS OF DICARBOXYLIC ACIDS FOR USE AS PIGMENT DISPERSANTS

(76) Inventors: Ronald J. Smith, 72 Fairview Ave., Woodcliff Lake, NJ (US) 07677; Maria K. Smith, 72 Fairview Ave., Woodcliff Lake, NJ (US) 07677

( * ) Notice: Subject to any disclaimer, the term of this patent is extended or adjusted under 35 U.S.C. 154(b) by 0 days.

This patent is subject to a terminal disclaimer.

(21) Appl. No.: 11/231,190

(22) Filed: Sep. 21, 2005

(65) Prior Publication Data
US 2006/0014978 A1    Jan. 19, 2006

Related U.S. Application Data

(63) Continuation-in-part of application No. 10/730,752, filed on Dec. 8, 2003, now Pat. No. 7,015,350.

(60) Provisional application No. 60/431,758, filed on Dec. 9, 2002.

(51) Int. Cl.
C07C 69/52 (2006.01)
C07C 69/34 (2006.01)
B41J 7/18 (2006.01)

(52) U.S. Cl. ............... 560/199; 560/198; 560/190; 400/401

(58) Field of Classification Search ............. 560/129, 560/201, 190, 193, 198
See application file for complete search history.

(56) References Cited

U.S. PATENT DOCUMENTS

2003/0114520 A1 * 6/2003 Pereira et al. ............... 514/532

* cited by examiner

*Primary Examiner*—Karl Puttlitz
(74) *Attorney, Agent, or Firm*—Michael E. Zall

(57) ABSTRACT

Novel mixed esters of dicarboxylic acids with monohydric fatty alcohols and propoxylated fatty alcohols show unexpected superior properties as pigment dispersants, especially for inorganic pigments used in foundations, make-ups, lipsticks and physical sunscreens. The compounds of the present invention show superior pigment wetting and dispersing properties, as demonstrated by their ability to form fluid, very high-solids dispersions, while exhibiting unusual emolliency and gloss formation.

The novel compounds of this invention have the following structural formula:

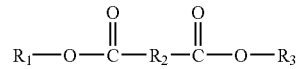

wherein $R_1$ is has the structural formula:

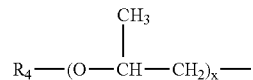

wherein:
$R_4$ is a saturated or unsaturated, substituted or unsubstituted aliphatic moiety containing from 4 to 24 carbon atoms;
X is an integer from 3 to 30;
$R_2$ is a saturated or unsaturated, substituted or unsubstituted aliphatic moiety which contains from 4 to 40 carbon atoms; and
$R_3$ is a saturated or unsaturated, straight chain or branched chain aliphatic moiety containing from 12 to 24 carbon atoms. The preferred compounds are Octyldodecyl PPG-3 Myristyl Ether Dilinoleate and Isostearyl PPG-4 Butyloctyl Ether Dilinoleate.

19 Claims, No Drawings

MIXED ESTERS OF DICARBOXYLIC ACIDS FOR USE AS PIGMENT DISPERSANTS

RELATED APPLICATIONS

This application is a continuation-in-part application of U.S. Ser. No. 10/730,752 filed on Dec. 08, 2003, now U.S. Pat. No. 7,015,350, which claims priority of Provisional Application Ser. No. 60/431,758 filed Dec. 09, 2002, the entire disclosures of which are incorporated herein by reference.

FIELD OF THE INVENTION

The present invention relates to novel mixed esters of polypropoxylated fatty alcohols and monohydric fatty alcohols with dicarboxylic fatty acids. These compounds exhibit unique pigment dispersion, emolliency and gloss-imparting properties. The fatty mixed esters of the present invention are particularly useful in the formulation of make-ups and other pigmented products, lotions, lipsticks, cold creams, skin moisturizers, sunscreen lotions, topical pharmaceutical products and cleansing creams. The present invention further relates to topical preparations incorporating the fatty mixed esters of the present invention.

BACKGROUND

A diverse range of formulations useful in personal care and pharmaceutical applications utilize inorganic pigments and other micronized inorganic oxides, such as physical sunscreen ingredients. Typically, these finely divided particulate products are dispersed within formulations by mixing, using either low-shear or high-shear methods. In order to make stable, cosmetically acceptable products, uniform dispersions must be produced, with all particles wetted out and which remain in suspension over a period of time without settling, jelling or agglomerating. Producing such stable suspensions has proved to be a challenge, although some successes have been achieved.

For example, U.S. Pat. No. 5,116,604 to Fogel describes the use of neopentanoate esters, in particular isoarchidyl neopentanoate, as cosmetic emollients for sunscreen products. U.S. Pat. No. 5,716,602 to Ulck describes sunscreens formulated to include a water resistance agent and an insect repellent. One form has in it an aqueous emulsion DEET, a sunscreen agent, an anionic surfactant, an alkylated PVP, and octyldodecyl neopentanoate. Both Fogel and Ulck use Octyldodecyl Neopentanoate.

U.S. Pat. No. 5,476,643 to Fogel describes the use of two specific neopentyl glycol diesters, as wetting, dispersing, spreading and detergent agents for micronized $TiO_2$, ZnO and other pigments. These esters, neopentyl glycol di-2-ethyl hexanoate and neopentyl glycol di-isostearate, are used in varying combinations and may also be used with an emulsifying agent for a water dispersible pigmented make-up cleaner composition.

Emollients such as $C_{12}$–$C_{15}$ Alkyl Benzoate (Finsolv TN, Finetex, Inc.) and Tridecyl Neopentanoate (TRIVENT NP-13) have also been employed with some success as dispersants for physical sunscreens, as have various glycols and propoxylates, such as PPG-3 Myristyl Ether. See for example, U.S. Pat. No. 5,928,631 to Lucas which describes a skin composition for controlling environmental malodors on the body. The composition comprises from about 0.1% to about 5%, by weight of a solubilized, water-soluble, uncomplexed cyclodextrin; from about 0.1% to about 36%, by weight of an oil phase selected from the group consisting of emollients, moisturizers, and skin protectants; one or more surfactants, and an aqueous carrier.

Several other possibly relevant US Patents are:

U.S. Pat. No. 4,830,768 to Reich, et al. discloses a fatty propoxylated ester of dicarboxylic acid and fatty alcohol with 1–15 units of propoxylation. Lubricating properties are claimed for non-topical preparations.

U.S. Pat. No. 5,693,316 to Pereira, et al. discloses a fatty alkoxylated ester of dicarboxylic acid and a stoichiometric excess of 1 of more polyalkoxylated fatty alcohols with emollient properties for topical preparations. The preparations include mineral oil as a second emollient.

U.S. Pat. No. 5,302,377 to Pereira, et al. discloses a fatty alkoxylated ester of tricarboxylic acid and a stoichiometric excess of 1 or more polyalkoxylated fatty alcohols with emollient properties for topical preparations. The preparations include mineral oil as a second emollient.

U.S. Pat. No. 5,455,025 to Pereira, et al. discloses fatty alkoxylated esters of tricarboxylic acid with a stoichiometric excess of 1 or more polyalkoxylated fatty alcohols having emollient properties for topical preparations.

U.S. Pat. No. 5,597,555 to Pereira, et al. discloses a fatty alkoxylated ester of dicarboxylic acid with a stoichiometric excess of 1 or more polyalkoxylated fatty alcohols with emollient properties for topical preparations.

U.S. Pat. No. 6,476,254 to Pereira, et al. discloses a fatty alkoxylated ester of dicarboxylic acid and fatty alcohol with pigment wetting/dispersant/emollient properties for topical preparations.

None of these references disclose mixed fatty acid esters of dicarboxylic acid and their use as effective pigment dispersants.

Thus there remains a need for superior dispersants with desirable esthetic properties for use in pigmented cosmetic compositions, particularly sunscreen formulations that contain physical sunscreens.

Additionally, since formulators often find it useful to fully disperse pigments, e.g., micronized metallic oxides, in a portion of the oil phase by high shear techniques such as milling, there is a need for forming oil phase dispersions which have a high solids content of pigments, particularly micronized metallic oxides, that are fluid.

SUMMARY OF THE INVENTION

We have now discovered that certain novel mixed esters produced by reacting dicarboxylic acids with monohydric fatty alcohols and propoxylated fatty alcohols show unusual, unexpectedly superior properties as pigment dispersants, especially for inorganic pigments used in foundations, make-ups, lipsticks and physical sunscreens. The compounds of the present invention show superior pigment wetting and dispersing properties, as demonstrated by their ability to form fluid, very high-solids dispersions, while exhibiting unusual emolliency and gloss formation.

The novel compounds of this invention have the following structural formula:

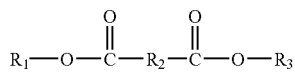

wherein $R_1$ has the structural formula:

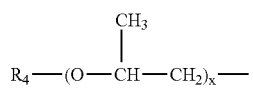

wherein:

$R_4$ is a saturated or unsaturated, substituted or unsubstituted aliphatic moiety containing from 4 to 24 carbon atoms;

X is an integer from 3 to 30;

$R_2$ is a saturated or unsaturated, substituted or unsubstituted aliphatic moiety which contains from 4 to 40 carbon atoms; and $R_3$ is a saturated or unsaturated, straight chain or branched chain aliphatic moiety containing from 12 to 24 carbon atoms.

The preferred compounds are Octyldodecyl PPG-3 Myristyl Ether Dilinoleate and Isostearyl PPG-4 Butyloctyl Ether Dilinoleate.

DETAILED DESCRIPTION OF INVENTION

The novel compounds of this invention are particularly useful in wetting and dispersing pigments, including such pigments as metallic oxides. The novel mixed esters of this invention are produced by the reaction of propoxylated fatty alcohols and monohydric fatty alcohols with dicarboxylic fatty acids. Preferably, the propoxylated fatty alcohols have a carbon chain length between 4 and 24 carbon atoms and a degree of propoxylation between 3 and 30, and most preferably between 3 and 15 units of propylene oxide.

It is additionally preferred that the diacid used in this invention is an aliphatic diacid having a carbon chain length between 4 and 40. The preferred fatty alcohols are chosen from a group having a carbon chain length between 12 and 24.

A preferred aliphatic diacid is dilinoleic acid and preferred propoxylated fatty alcohols are myristyl alcohol and butyloctanol. Preferred monohydric fatty alcohols are octyldodecanol and isostearyl alcohol.

The highly preferred compounds are Octyldodecyl PPG-3 Myristyl Ether Dilinoleate and Isostearyl PPG-4 Butyloctyl Ether Dilinoleate.

This invention is also directed to topical formulations which include the aforedescribed mixed esters, one or more active ingredients, and water. A second emollient agent of mineral oil, petrolatum and the like, may also be included. Suitable active ingredients for use in such topical preparations include organic sunscreens, physical sunscreens, self-tanning agents, pigments, opacifying agents, moisturizers, film-formers, thickening agents, emulsifiers, antiseptic agents, conditioning agents and deodorant actives.

These aforedescribed topical preparations, in addition to including the aforedescribed mixed esters of fatty polypropoxylated esters, may also include one or more active ingredients, water and an optional second emollient agent, and fragrances, humectants, protein derivatives, coloring agents, preservatives and the like, as well.

Preferred topical formulations in accordance with the present invention include the aforedescribed fatty mixed polypropoxylated diesters, either alone or in combination with a second emollient agent, in a range of from about 0.2% to about 20.0% by weight of the composition. The second emollient agent, when present, may be blended with the compounds of this invention in a ratio of about 3:1 by weight of the former to the latter.

EXAMPLES OF PREPARATION OF THE COMPOUNDS

The fatty alcohol, e.g., myristyl alcohol, is reacted with propylene oxide in the presence of an alkaline catalyst in a manner well known in the art, followed by neutralization with a suitable acid such as phosphoric acid. Either one or two equivalents of the resultant propoxylated fatty alcohol (e.g. PPG-3 Myristyl Ether) and one or two equivalents of the monohydric fatty alcohol, (e.g. octyldodecanol) are reacted in the conventional fashion with one mole of the dicarboxylic (e.g. dilinoleic acid). This is followed by neutralization with a suitable base such as sodium carbonate. The typical reaction is as follows:

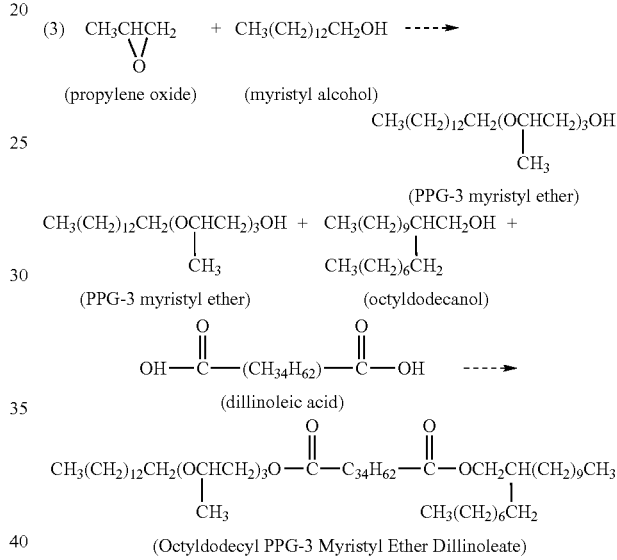

Preparation of Octyldodecyl PPG-3 Myristyl Ether Dilinoleate 3 moles (642 grams) of Myristyl Alcohol were charged to an autoclave, and 0.1% of Potassium Hydroxide was added as a catalyst. The autoclave was purged with Nitrogen and 9 moles (522 grams) of Propylene Oxide were added at a temperature of 150–160° C. and a pressure of 30–40 psi. At the completion of the additional reaction, the batch was cooled to 80° C. and neutralized with Phosphoric Acid. The resultant 1,164 grams of product, PPG-3 Myristyl Ether, a pale yellow liquid, was charged to a four-neck flask.

Three (3) moles (900 grams) of Octyldodecanol and Dilinoleic Acid were charged to the flask, along with a catalytic amount of methanesulfonic acid. The reaction mixture was heated with agitation to 150° C. under 28" Hg of vacuum until an acid value of less than 5 mg KOH was obtained. The reaction mixture was cooled to 80° C., washed with a dilute Sodium Carbonate solution sufficient to neutralize the residual acid present, followed by washing with water.

The ester layer was separated and heated under vacuum until a moisture content of less than 0.3% was obtained, followed by vacuum filtration. The resultant product, Octyldodecyl PPG-3 Myristyl Ether Dilinoleate, was a clear, pale yellow liquid, having an acid value of 0.32 mg KOH.

Preparation of Isostearyl PPG-4 Butyloctyl Ether Dilinoleate 4 moles (744 grams) of Butyloctanol were charged to an autoclave, and 0.1% of Potassium Hydroxide was added as catalyst. The autoclave was purged with Nitrogen and 16 moles (928 grams) of Propylene Oxide were added at a temperature of 150–160° C. and a pressure of 30–40 psi. Upon completion, the batch was cooled to 80° C. and neutralized with Phosphoric Acid. The resultant product, PPG-4 Butyloctyl Ether, was a very pale yellow liquid.

A four-neck flask was charged with 3 moles (1,254 grams) of PPG-4 Butyloctyl Ether, 3 moles of Isostearyl Alcohol (840 grams), along with 3 moles (1.755 grams) of Dilinoleic Acid.

A catalytic amount of p-Toluenesulfonic Acid was added and the reaction mixture was heated with agitation to 140° C. under 28" Hg of vacuum until an acid value of less than 5 mg KOH was obtained. The reaction mixture was cooled to 80° C., washed with a dilute Sodium Hydroxide solution sufficient to neutralize the residual acid present, followed by washing with water. The ester layer was separated and heated under vacuum until a moisture content of less than 0.2% was obtained, followed by vacuum filtration. The resultant product, Isostearyl PPG-4 Butyloctyl Ether Dilinoleate, was a clear very pale yellow liquid having an acid value of less than 0.1 mg KOH.

COMPARATIVE EXAMPLES

Comparisons were made between the compounds of the present invention and several common dispersants used in foundations and lipsticks for their ability to form fluid, high-solids dispersions.

The tests were performed by adding 10 grams of yellow iron oxide to 90 grams of the test dispersant in a beaker and mixing for 15 minutes with a Silverson mixer at 9,000 rpm. After 15 minutes, the sample was checked with a grind gauge to confirm full dispersion. The dispersion was cooled to room temperature and the viscosity was measured. Additional 2-gram increments of pigment were added, following the above procedure, until streaking was observed with the grind gauge or until a viscosity of 10,000 cps was reached.

a) With mineral oil the cut-off viscosity was exceeded at 10 grams of pigment.

b) With $C_{12}$–$C_{15}$ Alkyl Benzoate the cut-off viscosity was reached at about 11 grams of pigment.

c) With Isononyl Isononanoate the cut-off viscosity was reached at about 16 grams of pigment.

d) With castor oil the cut-off viscosity was reached at about 21 grams of pigment.

e) With Cyclomethicone the cut-off viscosity was reached at about 26 grams of pigment.

f) With Dioctyldodecyl Dimer Dilinoleate the cut-off viscosity was reached at about 34 grams of pigment.

g) With Octyldodecyl PPG-3 Myristyl Ether Dimer Dilinoleate the addition of about 66 grams of pigment remained below the cut-off viscosity, which measured at approximately 6,000 cps.

These comparisons demonstrate that a mixed ester of dicarboxylic acid with a fatty alcohol and a propoxylated fatty alcohol exhibit unusual pigment dispersant properties.

What is claimed is:

1. A compound of the following structural formula:

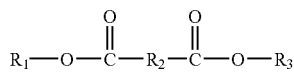

wherein $R_1$ has the structural formula:

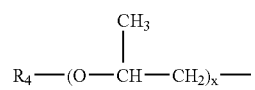

wherein:

$R_4$ is a saturated aliphatic moiety of from 4 to 24 carbon atoms;

X is an integer from 3 to 30;

$R_2$ is a saturated aliphatic moiety of from 4 to 40 carbon atoms; and

R3 is a saturated, straight chain or branched chain aliphatic moiety of from 12 to 24 carbon atoms.

2. The compound of claim 1 where $R_4$ is a saturated aliphatic moiety of 12 or 20 carbon atoms.

3. The compound of claim 1, where $R_2$ is a saturated aliphatic moiety of 34 carbon atoms.

4. The compound of claim 1, where X is 3 or 4.

5. The compound of claim 1 wherein $R_3$ is a saturated, branched chain aliphatic moiety of from 12 to 24 carbon atoms.

6. The compound of claim 1 wherein $R_3$ is a saturated branched chain aliphatic moiety of 12 or 20 carbon atoms.

7. The compound of claim 1, wherein $R_3$ is Octyldodecane.

8. The compound of claim 1, wherein $R_3$ is Isostearyl.

9. The compound Isostearyl PPG-4 Butyloctyl Ether Dilinoleate.

10. A cosmetically acceptable topical composition comprising a) water;

b) a cosmetically effective amount of at least one active ingredient selected from the group consisting of organic sunscreens, physical sunscreens, self tanning agents, pigments, opacifying agents, moisurizers, film formers, thickening agents, emulsifiers, conditioning agents and deodorant actives;

c) an amount of an inorganic micronized pigment, d) a dispersant emollient agent in sufficient amount to disperse such active ingredients and micronized pigments to produce a stable uniform dispersion, such agent being a compound of the following structural formula:

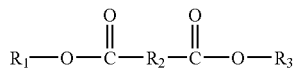

wherein $R_1$ has the structural formula:

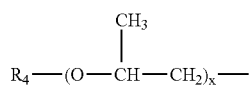

wherein:
- $R_4$ is a saturated aliphatic moiety of from 4 to 24 carbon atoms;
- X is an integer from 3 to 30;
- $R_2$ is a saturated aliphatic moiety of from 4 to 40 carbon atoms; and
- $R_3$ is a saturated straight chain or branched chain aliphatic moiety of from 12 to 24 carbon atoms.

11. The composition of claim 10 where $R_4$ is a saturated aliphatic moiety of 12 or 20 carbon atoms.

12. The composition of claim 10, where $R_2$ is a saturated aliphatic moiety of 34 carbon atoms.

13. The composition of claim 10, wherein X is 3 or 4.

14. The composition of claim 10, wherein $R_3$ is a saturated, branched chain aliphatic moiety of from 12 to 24 carbon atoms.

15. The composition of claim 10, wherein $R_3$ is a saturated branched chain aliphatic moiety of 12 or 20 carbon atoms.

16. The composition of claim 10, wherein $R_3$ is Octyldodecane.

17. The composition of claim 10, wherein $R_3$ is Isostearyl.

18. The composition of claim 10, wherein the emollient agent is Isostearyl PPG-4 Butyloctyl Ether Dilinoleate.

19. A method of dispersing an amount of an inorganic micronized pigment in a topical composition containing water and a cosmetically effective amount of at least one active ingredient selected from the group consisting of organic sunscreens, physical sunscreens, self tanning agents, pigments, opacifying agents, moisturizers, film formers, thickening agents, emulsifiers, conditioning agents and deodorant actives comprising: adding into the composition the inorganic micronized pigment and a dispersant emollient agent in sufficient amount to disperse such active ingredients and micronized pigment, such agent being a compound of the following structural formula:

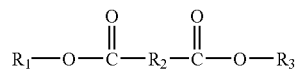

wherein $R_1$ has the structural formula:

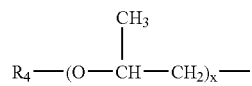

wherein:
- $R_4$ is a saturated aliphatic moiety of from 4 to 24 carbon atoms;
- X is an integer from 3 to 30;
- $R_2$ is a saturated aliphatic moiety of from 4 to 40 carbon atoms; and
- $R_3$ is a saturated straight chain or branched chain aliphatic moiety of from 12 to 24 carbon atoms,
- to produce a stable, cosmetically acceptable uniform dispersion is produced.

* * * * *